United States Patent
Franke et al.

(10) Patent No.: US 7,812,200 B2
(45) Date of Patent: Oct. 12, 2010

(54) PROCESS FOR PREPARING 1,2-PROPANEDIOL BY HYDROGENOLYSIS OF GLYCEROL

(75) Inventors: Oliver Franke, Munich (DE); Achim Stankowiak, Altoetting (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 12/446,805

(22) PCT Filed: Jun. 16, 2007

(86) PCT No.: PCT/EP2007/005325

§ 371 (c)(1),
(2), (4) Date: Apr. 23, 2009

(87) PCT Pub. No.: WO2008/049470

PCT Pub. Date: May 2, 2008

(65) Prior Publication Data

US 2010/0036175 A1   Feb. 11, 2010

(30) Foreign Application Priority Data

Oct. 27, 2007  (DE) .................. 10 2006 050 751

(51) Int. Cl.
*C07C 29/132* (2006.01)
(52) U.S. Cl. .................................... 568/861
(58) Field of Classification Search ............. 568/861
See application file for complete search history.

(56) References Cited

U.S. PATENT DOCUMENTS

| 4,642,394 A | 2/1987 | Che |
| 5,387,753 A | 2/1995 | Scarlett et al. |
| 5,616,817 A | 4/1997 | Schuster et al. |

FOREIGN PATENT DOCUMENTS

| CN | 101 012 149 A | | 8/2007 |
| DE | 43 02 464 A1 | | 8/1994 |
| DE | 44 42 124 A1 | | 5/1996 |
| EP | 0 523 015 A2 | | 1/1993 |
| EP | 0523015 A | * | 5/1993 |
| EP | 0 713 849 A1 | | 5/1996 |
| EP | 0713849 A1 | * | 5/1996 |
| WO | WO 2007/010299 A1 | | 1/2007 |

OTHER PUBLICATIONS

English Abstract for DE 43 02 464 A1, 1994.
English Abstract for CN 101 012 149 A, 2007.
International Search Report for PCT/EP2008/000255, dated Apr. 10, 2008.
International Search Report for PCT/EP2007/005325, dated Sep. 6, 2007.
International Preliminary Report on Patentability for PCT/EP2007/005325.

* cited by examiner

*Primary Examiner*—Elvis O Price
(74) *Attorney, Agent, or Firm*—Tod A. Waldrop

(57) ABSTRACT

The invention provides a process for preparing 1,2-propanediol, by reacting glycerol which has a purity of at least 95% by weight with hydrogen at a hydrogen pressure of from 20 to 100 bar and a temperature of from 180 to 240 DEG C. in the presence of a catalyst which comprises from 10 to 50% by weight of copper oxide and from 50 to 90% by weight of zinc oxide in an autoclave.

5 Claims, No Drawings

PROCESS FOR PREPARING 1,2-PROPANEDIOL BY HYDROGENOLYSIS OF GLYCEROL

The present invention relates to a process for preparing 1,2-propanediol from glycerol. 1,2-Propanediol is currently prepared on the industrial scale from propylene oxide by addition of water and used in a multitude of applications, for example as a constituent of brake fluids and hydraulic fluids, lubricants and antifreezes, in cosmetics, in the foods industry and as solvents for fats, oils, resins and dyes. Propylene oxide and hence also 1,2-propanediol are currently still prepared completely from fossil fuels. As a result of the constant demand for the use of renewable raw materials and the rising crude oil and falling glycerol prices, there is a great need to use glycerol, which is obtained as a by-product in large amounts in biodiesel production, as a starting material for suitable chemical reactions on the industrial scale.

The catalytic hydrogenation of glycerol to 1,2-propanediol has already been studied frequently.

DE-A-44 42 124 describes the catalytic hydrogenation of glycerol having a water content of up to 20% by weight to propylene glycol in a yield of 92%; the by-products obtained are n-propanol and lower alcohols. The complete conversion of glycerol is achieved through the use of a mixed catalyst composed of the metals cobalt, copper, manganese and molybdenum. The reaction conditions are within a pressure and temperature range from 100 to 700 bar and 180 to 270° C. Preferred hydrogenation conditions are 200 to 325 bar and 200 to 250° C. Disadvantages are that the conversion of glycerol is incomplete at lower pressures, and lower alcohols form to an increased extent at higher pressures.

U.S. Pat. No. 4,642,394 describes a process for catalytically hydrogenating glycerol with a catalyst consisting of tungsten and a group VIII metal. The reaction conditions are within the range from 100 psi to 15 000 psi and 75 to 250° C. Preferred process conditions are 100 to 200° C. and 200 to 10 000 psi. The reaction is carried out under basic conditions through the use of amines or amides as solvents. It is also possible to use metal hydroxides, metal carbonates or quaternary ammonium salts. The solvent is added in a concentration of 5 to 100 ml per gram of glycerol. To stabilize and activate the catalyst, carbon monoxide is used.

EP-A-0 523 015 describes the hydrogenation of glycerol over Cu/Zn catalysts, though very dilute aqueous solutions (glycerol content approx. 30% by weight) are employed, which become even more dilute as a result of the water of reaction which forms. To obtain 1,2-propanediol, a large amount of water therefore has to be distilled out of the product, which means a high energy expenditure and makes the process uneconomic. Moreover, the process is carried out at relatively high pressures of preferably 100-150 bar and high temperatures of 230-270° C. The conversion of glycerol is within the range from 8 to 100% at a selectivity for propylene glycol of 80 to 98%; the by-products formed are alcohols and ethylene glycol.

DE-A-43 02 464 describes a process in which glycerol is hydrogenated in continuous moue over a CuO/ZnO fixed bed catalyst. This process achieves complete hydrogenation of glycerol at 200° C.; the by-products formed are small amounts of low-hydricity alcohols and relatively large amounts (5.4% by weight) of unknown substances. The very high reaction pressure of 250 bar is likewise disadvantageous. At lower pressures (50-150 bar) and higher temperatures (240° C.), unknown substances (25-34% by weight) are formed to an increased extent, while the selectivity for 1,2-propanediol falls to 22-31% by weight.

There was thus a need for an improved process for preparing 1,2-propanediol from glycerol, which gives rise to 1,2-propanediol with high selectivity and high space-time yield, and thus does not have the disadvantages of the prior art.

It has been found that, surprisingly, 1,2-propanediol can be prepared by hydrogenating essentially pure glycerol over a copper oxide/zinc oxide catalyst in high yield and high selectivity. In the process according to the invention, with complete conversion of the glycerol, a selectivity for 1,2-propanediol of up to 98% is achieved; the only by-products detectable are monoethylene glycol (approx. 2%) and a small amount of n-propanol.

The invention provides a process for preparing 1,2-propanediol, by reacting glycerol which has a purity of at least 95% by weight with hydrogen at a hydrogen pressure of from 20 to 100 bar and a temperature of from 180 to 240° C. in the presence of a catalyst which comprises from 10 to 50% by weight of copper oxide and from 50 to 90% by weight of zinc oxide in an autoclave.

The catalyst used in the process according to the invention is preferably free of support material and contains preferably 30-35% by weight of copper oxide and preferably 65-70% by weight of zinc oxide. In a further preferred embodiment, copper oxide and zinc oxide add up to 100% by weight. A reduction and activation of the catalyst before the reaction can be undertaken in a hydrogen stream at 170-240° C., but is not required since it is activated very rapidly at the start of and later in the reaction.

The hydrogenation of glycerol is performed in the process according to the invention at hydrogen pressures of preferably 50-80 bar, and temperatures of preferably 200-220° C.

In the process according to the invention, the hydrogenation of glycerol of high purity of 99% by weight and higher is preferred.

When crude glycerol from the transesterification of fats and oils is used in the process according to the invention, it should appropriately be concentrated by distillation and freed of catalyst poisons, such as sulfuric acid, which is often used as a transesterification catalyst.

The process according to the invention has the advantage that a complete hydrogenation of the glycerol is achieved, the desired 1,2-propanediol reaction product being formed in high selectivity of up to 98% by weight. The only by-products detectable are monoethylene glycol and small amounts of n-propanol, which can be removed easily by distillation with the water of reaction. The product mixture obtained can, if required, either be used directly for chemical applications or be converted to pure 1,2-propanediol (>99.5% by weight) by further distillative purification.

The example which follows illustrates the invention:

EXAMPLE 1

Process for Preparing 1,2-propanediol by Hydrogenolysis of Glycerol Over a CuO/ZnO Catalyst A pressure autoclave with sparging stirrer was initially charged with 3750 g of 99.5% by weight glycerol and 150 g of a catalyst composed of 33% by weight of copper (as CuO) and 66% by weight of zinc (as ZnO). This catalyst had not been activated before the reaction. Thereafter, hydrogen was injected in the cold state up to a pressure of 30 bar and the autoclave was heated to 200° C. On attainment of this reaction temperature, the hydrogen pressure was increased to 50 bar and kept at this pressure by further injection over the course of the reaction. After 12 h, the autoclave was cooled and emptied, and the contents were removed from the catalyst.

The analysis was effected by means of GC. 97.7% by weight of 1,2-propanediol and 2.2% by weight of monoethylene glycol, and also 0.1% by weight of n-propanol, were found. Glycerol was no longer detectable. The water content of the reaction mixture was determined to be 18.9% by weight.

The invention claimed is:

1. A process for preparing 1,2-propanediol, comprising the step of reacting glycerol, which has a purity of at least 95% by weight, with hydrogen at a hydrogen pressure of from 20 to 100 bar and a temperature of from 180 to 240° C. in the presence of a catalyst which comprises from 10 to 50% by weight of copper oxide and from 50 to 90% by weight of zinc oxide, and wherein the catalyst is activated in a hydrogen stream at from 170 to 240° C. before the reaction, in an autoclave.

2. The process as claimed in claim 1, wherein the catalyst contains from 30 to 35% by weight of copper oxide and from 65 to 70% by weight of zinc oxide.

3. The process as claimed in claim 1, which is conducted at a hydrogen pressure of from 50 to 80 bar.

4. The process as claimed in claim 1, which is conducted at a temperature of from 200 to 220° C.

5. The process as claimed in claim 1, wherein the glycerol has a purity of 99% by weight or higher.

* * * * *